(12) United States Patent
Berzak et al.

(10) Patent No.: US 7,938,822 B1
(45) Date of Patent: May 10, 2011

(54) HEATING AND COOLING OF CRYOSURGICAL INSTRUMENT USING A SINGLE CRYOGEN

(75) Inventors: Nir Berzak, Givataim (IL); Simon Sharon, Ma'ayan Zvi (IL)

(73) Assignee: IceCure Medical Ltd., Caesarea (IL)

( * ) Notice: Subject to any disclaimer, the term of this patent is extended or adjusted under 35 U.S.C. 154(b) by 0 days.

(21) Appl. No.: 12/778,172

(22) Filed: May 12, 2010

(51) Int. Cl.
*A61B 18/02* (2006.01)
(52) U.S. Cl. .......... 606/20; 606/21; 606/22; 606/24; 606/25
(58) Field of Classification Search .......... 606/20–26
See application file for complete search history.

(56) References Cited

U.S. PATENT DOCUMENTS

| | | |
|---|---|---|
| 3,234,746 A | 2/1966 | Smith |
| 3,358,472 A | 12/1967 | Kipling |
| 3,664,344 A | 5/1972 | Bryne |
| 3,699,775 A | 10/1972 | Cowans |
| 3,712,306 A | 1/1973 | Bryne |
| 3,736,936 A | 6/1973 | Basiulis |
| 3,800,552 A | 4/1974 | Sollami |
| 3,862,630 A | 1/1975 | Balamuth |
| 3,882,849 A | 5/1975 | Jamshidi |
| 3,938,505 A | 2/1976 | Jamshidi |
| 3,971,383 A | 7/1976 | Van Gerven |
| 4,082,096 A | 4/1978 | Benson |
| 4,091,634 A | 5/1978 | Shepherd |
| 4,127,903 A | 12/1978 | Schachar |
| 4,200,104 A | 4/1980 | Harris |
| 4,211,231 A | 7/1980 | Rzasa |
| 4,279,626 A | 7/1981 | Buchmuller |
| 4,306,568 A | 12/1981 | Torre |
| 4,313,306 A | 2/1982 | Torre |
| 4,367,744 A | 1/1983 | Sole |
| 4,376,376 A * | 3/1983 | Gregory .......... 62/48.1 |
| 4,428,748 A | 1/1984 | Peyman |
| 4,463,458 A | 8/1984 | Seidner |
| 4,481,948 A | 11/1984 | Sole |
| 4,487,253 A | 12/1984 | Malek |
| 4,552,208 A | 11/1985 | Sorenson |
| 4,570,626 A | 2/1986 | Norris |
| 4,573,525 A | 3/1986 | Boyd |

(Continued)

FOREIGN PATENT DOCUMENTS

CA 2437079 6/2004

(Continued)

OTHER PUBLICATIONS

Verkin et al., Low Temperatures in Stomatology, Naukova Dumka, 1990, pp. 62-63, Kiev.

(Continued)

*Primary Examiner* — Roy D Gibson
*Assistant Examiner* — Amanda Scott
(74) *Attorney, Agent, or Firm* — The Law Office of Michael E. Kondoudis

(57) ABSTRACT

A cryosurgical system featuring both cooling and heating utilizing a single type of cryogen but from two different sources. The liquid cryogen cools the tip of a cryosurgical instrument in the cryosurgical system, such as a cryoprobe or cryocatheter. The gaseous cryogen is further heated by a heating element, preferably an electrical heating element, supplying the heating needed for the thaw and release parts of the cryo treatment procedure. Thus, the cryosurgical system supports the freeze/thaw cycle of the operation of the cryosurgical instrument.

15 Claims, 14 Drawing Sheets

U.S. PATENT DOCUMENTS

| | | | |
|---|---|---|---|
| 4,611,654 A | 9/1986 | Buchsel | |
| 4,617,018 A | 10/1986 | Nishi | |
| 4,676,225 A | 6/1987 | Bartera | |
| 4,726,194 A | 2/1988 | Mackay et al. | |
| 4,765,396 A | 8/1988 | Seidenberg | |
| 4,770,171 A | 9/1988 | Sweren | |
| 4,802,475 A | 2/1989 | Weshahy | |
| 4,831,856 A | 5/1989 | Gano | |
| 4,946,460 A * | 8/1990 | Merry et al. | 606/24 |
| 5,026,387 A | 6/1991 | Thomas | |
| 5,047,043 A | 9/1991 | Kubota | |
| 5,108,390 A | 4/1992 | Potocky | |
| 5,147,355 A | 9/1992 | Friedman | |
| 5,188,102 A | 2/1993 | Idemoto | |
| 5,214,925 A | 6/1993 | Hoy | |
| 5,222,937 A | 6/1993 | Kagawa | |
| 5,224,943 A | 7/1993 | Goddard | |
| 5,243,826 A | 9/1993 | Longsworth | |
| 5,254,082 A | 10/1993 | Takase | |
| 5,254,116 A | 10/1993 | Baust | |
| 5,261,923 A | 11/1993 | Soares | |
| 5,263,957 A | 11/1993 | Davison | |
| 5,264,116 A | 11/1993 | Apelian | |
| 5,275,595 A | 1/1994 | Dobak | |
| 5,281,215 A | 1/1994 | Milder | |
| 5,295,484 A | 3/1994 | Marcus | |
| 5,324,286 A | 6/1994 | Fowle | |
| 5,330,745 A | 7/1994 | Mcdow | |
| 5,334,181 A * | 8/1994 | Rubinsky et al. | 606/22 |
| 5,342,380 A | 8/1994 | Hood | |
| 5,361,591 A | 11/1994 | Caldwell | |
| 5,391,144 A | 2/1995 | Sakurai | |
| 5,411,374 A | 5/1995 | Gram | |
| 5,417,073 A | 5/1995 | James | |
| 5,423,807 A | 6/1995 | Milder | |
| 5,429,138 A | 7/1995 | Jamshidi | |
| 5,438,837 A | 8/1995 | Caldwell | |
| 5,441,512 A | 8/1995 | Muller | |
| 5,445,462 A | 8/1995 | Johnson | |
| 5,452,582 A | 9/1995 | Longsworth | |
| 5,488,831 A | 2/1996 | Griswold | |
| 5,516,505 A | 5/1996 | Mcdow | |
| 5,520,682 A | 5/1996 | Baust | |
| 5,526,821 A | 6/1996 | Jamshidi | |
| 5,547,473 A | 8/1996 | Peyman | |
| 5,573,532 A | 11/1996 | Chang | |
| 5,600,143 A | 2/1997 | Roberts | |
| 5,647,868 A | 7/1997 | Chinn | |
| 5,654,279 A | 8/1997 | Rubinsky | |
| 5,658,276 A | 8/1997 | Griswold | |
| 5,674,218 A | 10/1997 | Rubinsky | |
| 5,683,592 A | 11/1997 | Bartholomew et al. | |
| 5,687,776 A | 11/1997 | Forgash | |
| 5,716,353 A | 2/1998 | Matsuura | |
| 5,720,743 A | 2/1998 | Bischof | |
| 5,728,130 A | 3/1998 | Ishikawa | |
| 5,735,845 A | 4/1998 | Zupkas | |
| 5,771,946 A | 6/1998 | Kooy | |
| 5,787,940 A | 8/1998 | Bonn | |
| 5,800,448 A | 9/1998 | Banko | |
| 5,800,487 A | 9/1998 | Mikus | |
| 5,814,040 A | 9/1998 | Nelson | |
| 5,868,673 A | 2/1999 | Vesely | |
| 5,885,276 A | 3/1999 | Ammar | |
| 5,899,897 A | 5/1999 | Rabin | |
| 5,906,612 A | 5/1999 | Chinn | |
| 5,906,628 A | 5/1999 | Miyawaki | |
| 5,910,104 A * | 6/1999 | Dobak et al. | 600/121 |
| 5,921,982 A | 7/1999 | Lesh | |
| 5,976,092 A | 11/1999 | Chinn | |
| 5,976,505 A | 11/1999 | Henderson | |
| 5,992,158 A | 11/1999 | Goddard | |
| 6,012,453 A | 1/2000 | Tsais | |
| 6,024,750 A | 2/2000 | Mastri | |
| 6,027,499 A | 2/2000 | Johnston | |
| 6,032,068 A | 2/2000 | Daniel | |
| 6,032,675 A | 3/2000 | Rubinsky | |
| 6,035,657 A | 3/2000 | Dobak | |
| 6,036,667 A | 3/2000 | Manna | |
| 6,039,730 A | 3/2000 | Rabin | |
| 6,041,787 A | 3/2000 | Rubinsky | |
| 6,042,342 A | 3/2000 | Orian | |
| 6,053,906 A | 4/2000 | Honda | |
| 6,059,820 A | 5/2000 | Baronov | |
| 6,063,098 A | 5/2000 | Houser | |
| 6,095,149 A | 8/2000 | Sharkey | |
| 6,142,991 A | 11/2000 | Schatzberger | |
| 6,152,894 A | 11/2000 | Kubler | |
| 6,182,666 B1 | 2/2001 | Dobak | |
| 6,200,308 B1 | 3/2001 | Pope | |
| 6,206,832 B1 | 3/2001 | Downey | |
| 6,212,904 B1 | 4/2001 | Arkharov | |
| 6,216,029 B1 | 4/2001 | Paltieli | |
| 6,235,018 B1 | 5/2001 | LePivert | |
| 6,237,355 B1 | 5/2001 | Li | |
| 6,251,105 B1 | 6/2001 | Mikus | |
| 6,270,494 B1 | 8/2001 | Kovalcheck | |
| 6,280,407 B1 | 8/2001 | Manna | |
| 6,354,088 B1 | 3/2002 | Emmer | |
| 6,355,033 B1 | 3/2002 | Moorman et al. | |
| 6,358,264 B2 | 3/2002 | Banko | |
| 6,379,348 B1 | 4/2002 | Onik | |
| 6,383,180 B1 | 5/2002 | Lalonde | |
| 6,383,181 B1 | 5/2002 | Johnston | |
| 6,411,852 B1 | 6/2002 | Danek | |
| 6,413,263 B1 | 7/2002 | Lobdill | |
| 6,423,009 B1 | 7/2002 | Downey | |
| 6,432,102 B2 | 8/2002 | Joye | |
| 6,457,212 B1 | 10/2002 | Craig | |
| 6,468,268 B1 | 10/2002 | Abboud | |
| 6,468,269 B1 | 10/2002 | Korpan | |
| 6,471,217 B1 | 10/2002 | Hayfield | |
| 6,482,178 B1 | 11/2002 | Andrews | |
| 6,497,714 B1 | 12/2002 | Ishikawa | |
| 6,500,109 B2 | 12/2002 | Tokita | |
| 6,503,246 B1 | 1/2003 | Har-Shai | |
| 6,508,814 B2 | 1/2003 | Tortal | |
| 6,513,336 B2 | 2/2003 | Zurecki | |
| 6,547,784 B1 | 4/2003 | Thompson | |
| 6,551,309 B1 | 4/2003 | LePivert | |
| 6,562,030 B1 | 5/2003 | Abboud | |
| 6,565,556 B1 | 5/2003 | Korpan | |
| 6,581,390 B2 | 6/2003 | Emmer | |
| 6,582,426 B2 | 6/2003 | Moorman | |
| 6,631,615 B2 | 10/2003 | Drube | |
| 6,640,556 B2 | 11/2003 | Ursan | |
| 6,659,730 B2 | 12/2003 | Gram | |
| 6,659,956 B2 | 12/2003 | Barzell et al. | |
| 6,672,095 B1 | 1/2004 | Luo | |
| 6,678,621 B2 | 1/2004 | Wiener | |
| 6,682,525 B2 | 1/2004 | Lalonde | |
| 6,698,423 B1 | 3/2004 | Honkonen | |
| 6,702,761 B1 | 3/2004 | Damadian | |
| 6,761,715 B2 | 7/2004 | Carroll | |
| 6,765,333 B2 | 7/2004 | Mariaucue | |
| 6,768,917 B1 | 7/2004 | Van Vaals | |
| 6,772,766 B2 | 8/2004 | Gallo | |
| 6,786,902 B1 | 9/2004 | Rabin | |
| 6,824,543 B2 | 11/2004 | Lentz | |
| 6,852,706 B1 | 2/2005 | Heber-Katz | |
| 6,858,025 B2 | 2/2005 | Maurice | |
| 6,869,439 B2 | 3/2005 | White | |
| 6,889,695 B2 | 5/2005 | Pankratov | |
| 6,898,940 B2 | 5/2005 | Gram | |
| 6,908,472 B2 | 6/2005 | Wiener | |
| 6,910,510 B2 | 6/2005 | Gale | |
| 6,913,604 B2 | 7/2005 | Mihalik | |
| 6,932,771 B2 | 8/2005 | Whitmore | |
| 6,936,045 B2 | 8/2005 | Yu | |
| 6,942,659 B2 | 9/2005 | Lehmann | |
| 6,951,569 B2 | 10/2005 | Nohilly | |
| 6,954,977 B2 | 10/2005 | Maguire | |
| 6,995,493 B2 | 2/2006 | Isoda | |
| 7,001,378 B2 | 2/2006 | Yon | |
| 7,025,762 B2 | 4/2006 | Johnston | |
| 7,025,767 B2 | 4/2006 | Schaefer | |
| 7,071,690 B2 | 7/2006 | Butts | |

| | | |
|---|---|---|
| 7,081,111 B2 | 7/2006 | Svaasand |
| 7,101,367 B2 | 9/2006 | Xiao et al. |
| 7,128,739 B2 | 10/2006 | Prakash et al. |
| 7,137,978 B2 | 11/2006 | Levin |
| 7,144,228 B2 | 12/2006 | Emmer |
| 7,151,374 B2 | 12/2006 | Doty |
| 7,160,291 B2 | 1/2007 | Damasco |
| 7,160,292 B2 | 1/2007 | Moorman |
| 7,165,422 B2 | 1/2007 | Little |
| 7,189,228 B2 | 3/2007 | Eum |
| 7,207,985 B2 | 4/2007 | Duong |
| 7,213,400 B2 | 5/2007 | Dickerson |
| 7,223,080 B2 | 5/2007 | Duron |
| 7,250,046 B1 | 7/2007 | Fallat |
| 7,252,648 B2 | 8/2007 | Honda |
| 7,255,693 B1 | 8/2007 | Johnston |
| 7,273,479 B2 * | 9/2007 | Littrup et al. .................. 606/21 |
| 7,278,991 B2 | 10/2007 | Morris |
| 7,280,623 B2 | 10/2007 | Gupta |
| 7,282,919 B2 | 10/2007 | Doty |
| 7,288,089 B2 | 10/2007 | Yon |
| 7,318,327 B2 | 1/2008 | Dickerson |
| 7,344,530 B2 | 3/2008 | Bischoff |
| 7,344,531 B2 | 3/2008 | Bischoff |
| 7,354,434 B2 | 4/2008 | Zvuloni |
| 7,361,187 B2 | 4/2008 | Duong |
| 7,381,207 B2 | 6/2008 | Duong |
| 7,425,211 B2 | 9/2008 | Levin et al. |
| 7,458,968 B2 | 12/2008 | Carroll |
| 7,481,806 B2 | 1/2009 | Levin |
| 7,485,117 B2 | 2/2009 | Damasco |
| 7,498,812 B2 | 3/2009 | Doty |
| 7,510,554 B2 | 3/2009 | Duong |
| 7,563,260 B2 | 7/2009 | Whitmore |
| 7,731,711 B2 | 6/2010 | Levin |
| 7,803,154 B2 | 9/2010 | Toubia et al. |
| 2001/0047129 A1 | 11/2001 | Hall et al. |
| 2002/0016540 A1 | 2/2002 | Mikus et al. |
| 2002/0022832 A1 | 2/2002 | Mikus |
| 2002/0040220 A1 | 4/2002 | Zvuloni et al. |
| 2002/0077654 A1 | 6/2002 | Javier |
| 2002/0085921 A1 | 7/2002 | Gram |
| 2002/0144509 A1 | 10/2002 | Chalk |
| 2002/0156469 A1 | 10/2002 | Yon |
| 2002/0157402 A1 | 10/2002 | Drube |
| 2002/0160640 A1 | 10/2002 | Korpan |
| 2002/0161385 A1 | 10/2002 | Wiener |
| 2003/0060762 A1 | 3/2003 | Zvuloni |
| 2003/0079480 A1 | 5/2003 | Emmer |
| 2003/0126867 A1 | 7/2003 | Drube |
| 2003/0135119 A1 | 7/2003 | Lee et al. |
| 2003/0181897 A1 | 9/2003 | Thomas |
| 2003/0220635 A1 | 11/2003 | Knowlton |
| 2004/0024391 A1 | 2/2004 | Cytron |
| 2004/0055316 A1 | 3/2004 | Emmer et al. |
| 2004/0078033 A1 * | 4/2004 | Levin ........................... 606/20 |
| 2004/0215178 A1 | 10/2004 | Maurice |
| 2005/0016185 A1 | 1/2005 | Emmer |
| 2005/0038422 A1 | 2/2005 | Maurice |
| 2005/0056027 A1 | 3/2005 | White |
| 2005/0086949 A1 | 4/2005 | Noble |
| 2005/0106153 A1 | 5/2005 | Nordouist |
| 2005/0177147 A1 | 8/2005 | Vancelette |
| 2005/0192564 A1 | 9/2005 | Cosman et al. |
| 2005/0214268 A1 | 9/2005 | Cavanagh |
| 2005/0274142 A1 | 12/2005 | Corey |
| 2006/0049274 A1 | 3/2006 | Hume |
| 2006/0053165 A1 | 3/2006 | Hume |
| 2006/0079867 A1 | 4/2006 | Berzak |
| 2006/0122590 A1 | 6/2006 | Bliweis |
| 2006/0155267 A1 | 7/2006 | Berzak |
| 2006/0155268 A1 | 7/2006 | Amir |
| 2006/0264920 A1 | 11/2006 | Duong |
| 2006/0293647 A1 | 12/2006 | McRae |
| 2007/0000259 A1 | 1/2007 | Brook |
| 2007/0093710 A1 | 4/2007 | Maschke |
| 2007/0129626 A1 | 6/2007 | Mahesh |
| 2007/0129629 A1 | 6/2007 | Beauregard |
| 2007/0149959 A1 | 6/2007 | DeLonzor |
| 2007/0166171 A1 | 7/2007 | Kondo |
| 2007/0167939 A1 | 7/2007 | Duong |
| 2007/0276360 A1 | 11/2007 | Johnston |
| 2008/0027419 A1 | 1/2008 | Hamel |
| 2008/0051774 A1 | 2/2008 | Ofir |
| 2008/0051776 A1 | 2/2008 | Bliweis |
| 2008/0115509 A1 | 5/2008 | Gullickson |
| 2008/0119834 A1 | 5/2008 | Vancelette |
| 2008/0119838 A1 | 5/2008 | Vancelette |
| 2008/0319433 A1 | 12/2008 | Geiselhart |
| 2009/0011032 A1 | 1/2009 | LePivert |

FOREIGN PATENT DOCUMENTS

| | | |
|---|---|---|
| DE | 202004008875 U1 | 8/2004 |
| DE | 102005050344 | 5/2007 |
| EP | 0292922 B1 | 11/1988 |
| EP | 395307 A2 | 10/1990 |
| EP | 570301 | 11/1993 |
| EP | 955012 | 11/1999 |
| EP | 919197 B1 | 2/2005 |
| GB | 1108905 | 4/1968 |
| GB | 1402737 | 8/1975 |
| GB | 1473856 | 5/1977 |
| GB | 1534472 | 12/1978 |
| GB | 2336781 | 11/1999 |
| GB | 2409815 A1 | 7/2005 |
| JP | 2004041428 A2 | 2/2004 |
| JP | 2007144180 A2 | 6/2007 |
| JP | 2007167100 | 7/2007 |
| WO | WO8303961 A1 | 11/1983 |
| WO | WO9637158 A1 | 11/1996 |
| WO | WO9639960 A1 | 12/1996 |
| WO | WO9947876 A1 | 9/1999 |
| WO | WO0137919 A2 | 5/2001 |
| WO | WO0141683 A2 | 6/2001 |
| WO | WO0197702 | 12/2001 |
| WO | WO0202026 A1 | 1/2002 |
| WO | WO03015651 A1 | 2/2003 |
| WO | WO2004051409 A2 | 8/2004 |
| WO | WO0189183 A1 | 10/2004 |
| WO | WO2004060465 | 2/2005 |
| WO | WO2004093635 A2 | 6/2005 |
| WO | WO2005098308 A1 | 10/2005 |
| WO | WO2005000106 A2 | 12/2005 |
| WO | WO2006116457 A2 | 11/2006 |
| WO | WO2006127467 | 11/2006 |
| WO | WO2007028232 A1 | 3/2007 |
| WO | WO2007086056 A2 | 8/2007 |
| WO | WO2007129308 | 11/2007 |
| WO | WO 2009090647 A2 * | 7/2009 |

OTHER PUBLICATIONS

International Search Report and Written Opinion dated Nov. 5, 2008 in corresponding International Application No. PCT/IL2008/000794.

Qi et al., Development and performance test of a cryoprobe with heat transfer configuration enhancement, Cryogenics, 2006, pp. 881-887, vol. 46, Elsevier.

International Search Report dated Mar. 25, 2010 in corresponding International Application No. PCT/IB2009/052615.

International Search Report and Written Opinion dated Jul. 23, 2009 in corresponding International Application No. PCT/IL2009/000062.

International Search Report and Written Opinion dated Dec. 22, 2008 in corresponding International Application No. PCT/IL2008/001114.

International Search Report and Written Opinion dated Sep. 4, 2009 in corresponding International Application No. PCT/IB2009/051532.

Office Action dated Jan. 22, 2010 in Application No. EP 07805563.9.

International Search Report and Written Opinion dated Nov. 28, 2008 in corresponding International Application No. PCT/IL2008/000943.

International Search Report and Written Opinion dated Jan. 29, 2008 in corresponding International Application No. PCT/IL2007/001103.

International Search Report and Written Opinion dated Jan. 30, 2008 in corresponding International Application No. PCT/IL2007/001142.

International Search Report and Written Opinion dated Nov. 6, 2007 in corresponding International Application No. PCT/IL2007/000974.

Qi et al., Flow boiling of liquid nitrogen in micro-tubes: Part I—onset of nucleate boiling, two phase flow instability and two phase flow drop, International Journal of Heat and Mass Transfer, 2007, pp. 4999-5016, vol. 50, Elsevier.

Qi et al., Flow boiling of liquid nitrogen in micro-tubes: Part II—heat transfer characteristics and critical heat flux, International Journal of Heat and Mass Transfer, 2007, pp. 5017-5030, vol. 50, Elsevier.

Zhang et al., Two phase flow characteristics of liquid nitrogen in vertically upward 0.5 and 1.0 mm micro-tubes: Visualization studies, Cryogenics, 2009, pp. 565-575, vol. 49, Elsevier.

International Search Report and Written Opinion dated Aug. 24, 2010 in corresponding International Application PCT/US2010/34467.

U.S. Appl. No. 12/360,221, filed Jan. 27, 2009, Levin, Arbel Medical Ltd.

U.S. Appl. No. 11/851,055, filed Sep. 6, 2007, Toubia et al., Arbel Medical Ltd.

U.S. Appl. No. 12/017,035, filed Jan. 20, 2008, Toubia et al., Arbel Medical Ltd.

U.S. Appl. No. 11/763,093, filed Jun. 14, 2007, Levin et al., Arbel Medical Ltd.

U.S. Appl. No. 12/278,733, filed Nov. 5, 2008, Levin et al., Arbel Medical Ltd.

U.S. Appl. No. 11/857,085, filed Sep. 18, 2007, Levin et al., Arbel Medical Ltd.

U.S. Appl. No. 12/668,428, filed Sep. 7, 2010, Levin et al.

U.S. Appl. No. 12/673,506, filed Feb. 15, 2010, Levin et al.

U.S. Appl. No. 12/237,805, filed Sep. 25, 2008, Levin et al., Arbel Medical Ltd.

U.S. Appl. No. 12/313,611, filed Nov. 21, 2008, Toubia et al., Arbel Medical Ltd.

U.S. Appl. No. 12/812,819, filed Sep. 29, 2010, Toubia et al., IceCure Medical Ltd.

U.S. Appl. No. 12/988,233, filed Oct. 15, 2010, Toubia et al., Arbel Medical Ltd.

U.S. Appl. No. 12/611,938, filed Nov. 4, 2009, Levin.

U.S. Appl. No. 12/731,219, filed Mar. 25, 2010, Berzak et al., IceCure Medical Ltd.

U.S. Appl. No. 12/700,761, filed Feb. 5, 2010, Levin.

U.S. Appl. No. 12/846,047, filed Jul. 29, 2010, Berzak et al., IceCure Medical Ltd.

* cited by examiner

HEATING AND COOLING OF CRYOSURGICAL INSTRUMENT USING A SINGLE CRYOGEN

BACKGROUND

1. Technical Field

Embodiments of the present invention relate generally to cryosurgical equipment, and, more particularly, to the heating and cooling of cryoprobes or cryocatheters.

2. Description of Related Art

Cryoprobes that utilize a change of phase of a fluid cryogen, when this liquid cryogen is supplied from an external source into the cryoprobe tip, are known for performing cryosurgical procedures. Generally, a cryogen is delivered into a cryoprobe in the form of either a liquid and or two-phase fluid. The liquid phase of the delivered cryogen then cools the tip (distal section of the cryoprobe), by total or partial evaporation.

It can be advantageous to be able to both heat and cool the cryoprobe, in order to increase the efficacy of ablation. Most cryoablation treatments feature two cycles of cooling, separated by a thawing cycle, for increased efficacy, because the greatest damage to the tissue occurs during either a rapid decrease or a rapid increase in temperature, when the tissue goes through a phase change. A heating cycle therefore improves this phenomenon during thawing. The need for heating at the end of the treatment is twofold, the rapid heating improves the efficiency of the treatment, and the probe can be easily released from the tissue shortening the total procedure time.

Some compressed gases, such as helium, heat upon expansion. That is why helium is extensively used in Joules-Thomson processes.

U.S. Patent Publication No. 20060122590 discloses a device for both heating and cooling a cryoprobe, using a single source of gas, in Joules-Thomson process. This device, however, is based on the use of adiabatic expansion of high pressure Argon for cooling, and reducing the high pressure to reduce this cooling phenomenon to a minimum and heating the low pressure Argon.

BRIEF SUMMARY

The background art does not provide a solution that overcomes the challenge of providing both efficient and sufficient cooling and heating to the tip.

Embodiments of the present invention meet this challenge by providing a cryosurgical system featuring both cooling and heating utilizing a single type of cryogen but from two different sources. The liquid cryogen cools the tip of a cryosurgical instrument in the cryosurgical system, such as a cryoprobe or cryocatheter. The gaseous cryogen is further heated by a heating element, preferably an electrical heating element, supplying the heating needed for the thaw and release parts of the cryo treatment procedure. Thus, the cryosurgical system supports the freeze/thaw cycle of the operation of the cryosurgical instrument.

Illustrative embodiments of the present invention may variously provide a cryosurgical system with cryoprobe tip, which is situated near or in a cryogen supply passage of the cryoprobe and which, among many advantages, solves the above technical problem.

One aspect of the present invention provides a cryosurgical system, comprising: a cryosurgical instrument including a tip that is cooled by a cryogen in a fluid state and warmed by a same type of cryogen in a heated gaseous state; a fluid cryogen source that supplies a liquid cryogen to the cryosurgical instrument; and a gaseous cryogen source that supplies a gaseous cryogen to the cryosurgical instrument; and a heating element that selectively heats the gaseous cryogen. The gaseous cryogen and the fluid cryogen are not supplied to the cryosurgical instrument simultaneously but rather are supplied sequentially, such that wherein said fluid cryogen source is in fluid communication with the cryosurgical instrument, said gaseous cryogen source is not in fluid communication with the cryosurgical instrument; and such that wherein said gaseous cryogen source is in fluid communication with the cryosurgical instrument, said fluid cryogen source is not in fluid communication with the cryosurgical instrument. The gaseous cryogen source and the liquid cryogen source supply a same type of cryogen.

Another aspect of the present invention provides a cryosurgical system, comprising: a first source of a cryogen, the first source providing the cryogen is a gaseous phase; a second source of the cryogen, the second source providing the cryogen in a liquid phase; a cryogen heating section that selectively heats provided gaseous phase cryogen; and a cryosurgical instrument having a tip and receiving provided cryogen in a two-phase state. The provided cryogen in the liquid phase cools the tip. The provided cryogen, after being heated by the heating section, warms the tip. The heating and cooling of the tip are achieved using only the provided cryogen.

Yet another aspect of the present invention provides a system, comprising: a cryosurgical instrument having a tip; a first container storing a cryogen in a gaseous state; a second container storing the cryogen in a liquid state; and a gaseous cryogen heater that selectively heats the gaseous cryogen as it travels from the first container to the cryosurgical device. The heated gaseous cryogen is joined with liquid cryogen as it travels to the cryosurgical device. The liquid cryogen and heated gaseous cryogen cooperate to selectively heat and/or cool the tip.

Still another aspect of the present invention provides a cryosurgical system, comprising: a cryosurgical instrument having a tip that is warmed by heated gaseous cryogen and cooled by liquid cryogen; means for supplying a cryogen in a gaseous phase; means for supplying the cryogen in a liquid phase; means for mixing together supplied gaseous cryogen and supplied liquid cryogen so as to deliver to the cryosurgical instrument a two phase cryogen that includes cryogen in both liquid and gaseous phases; and means for selectively heating the gaseous cryogen.

These, additional, and/or other aspects and/or advantages of the present invention are: set forth in the detailed description which follows; possibly inferable from the detailed description; and/or learnable by practice of the present invention.

BRIEF DESCRIPTION OF THE DRAWINGS

The present invention will be more readily understood from the detailed description of embodiments thereof made in conjunction with the accompanying drawings of which:

FIG. 5b is a cross-sectional view of the first exemplary cryosurgical instrument of FIG. 5a take along line I-I of FIG. 5a;

FIG. 5c is a perspective view of a heat exchanging element of the cryosurgical instrument of FIG. 5a;

FIG. 6b is a cross-sectional view of the first exemplary cryosurgical instrument of FIG. 6a take along line II-II of FIG. 6a;

FIG. 7b is a cross-sectional view of the third exemplary cryosurgical instrument of FIG. 7a take along line III-III of FIG. 7a;

FIG. 7c is a perspective view of a heat exchanging element of the cryosurgical instrument of FIG. 7a.

DETAILED DESCRIPTION

Figure 1:
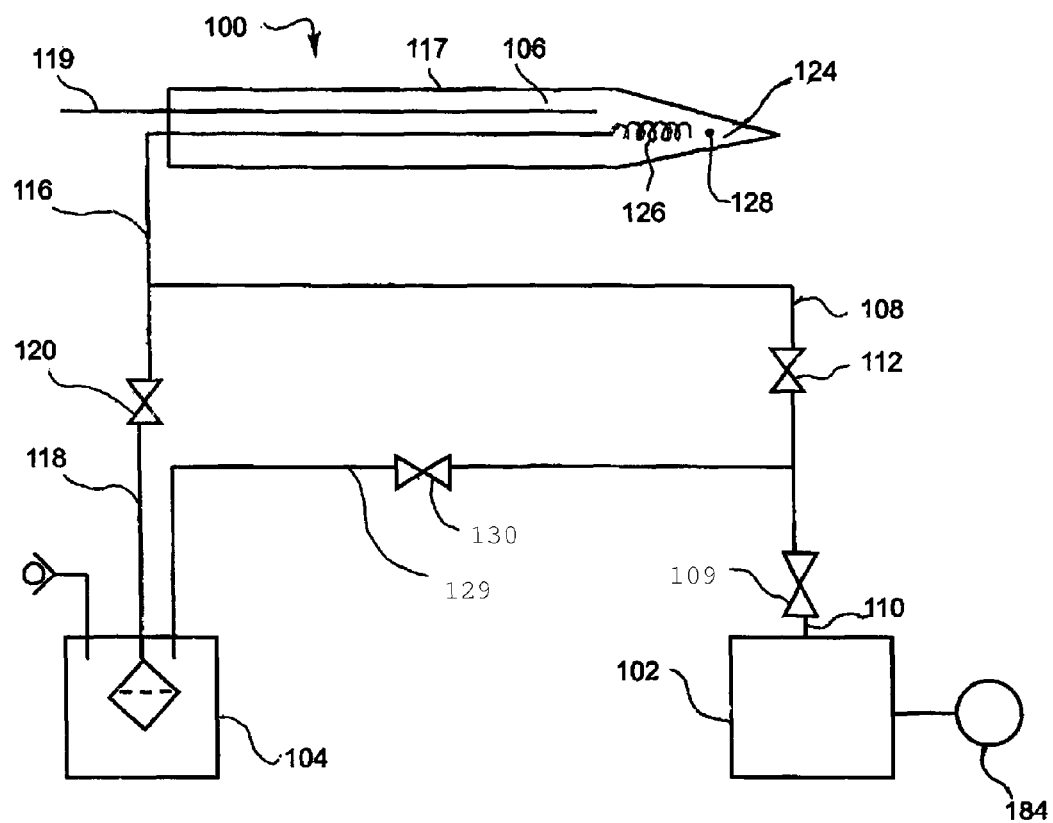
FIG. 1 is a schematic diagram of a cryosurgical system with cryosurgical instrument, consistent with an embodiment of the present invention, in which the heating element is inside of the cryosurgical instrument.

Reference will now be made in detail to embodiments of the present invention, examples of which are illustrated in the accompanying drawings, wherein like reference numerals refer to the like elements throughout. The embodiments are described below to explain the present invention by referring to the figures.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

The term "cryosurgical system" refers herein to any type of cryosystem consist of a source of cryogenic material, and including but not limited to cryoprobes and cryocatheters, for the purpose of cryoablation procedure. Although the description centers on cryoprobes, this is for the purpose of illustration only and is without any intention of being limiting.

Referring to FIG. 1, there is illustrated a system 100 comprising a gaseous cryogen source 102, a liquid cryogen source 104, and a cryosurgical instrument 106.

A salient feature of the system 100 is a heating element 126 disposed in the tip 124 that warms cryogen gas flowing in the tip, during thawing part of the procedure. One particularly advantageous type of heating element is an electrical heating element.

The cryosurgical instrument 106 includes an outer shaft 117 surrounding both inlet lumen 116 and an exhaust lumen 119. Inlet lumen 116 preferably includes two separated portions (shown in FIGS. 5a, 6a, and 7a). A first separated portion is a gas portion that is preferably located adjacent an exhaust lumen 119, which is preferably located between an outer wall of inlet lumen 116 and an inner wall of outer shaft 117. A second separated portion is an exhaust lumen 119 that may optionally be defined by the outer wall of inlet lumen 116 and the inner wall of outer shaft 117, or alternatively may be defined by a separate wall and/or by an outer wall of the gas portion of inlet lumen 116 (shown in 5a, 6a, and 7a).

The inlet lumen 116 receives the two-phase cryogen fluid from cryogen source 104. The liquid portion of inlet lumen 116 is in communication with tip 124 of cryosurgical instrument 106, such that cryogen enters through the inlet lumen 116 and then flows to tip 124, thereby cooling tip 124 and causing an ice ball to form.

Each cryogen source 102 and 104 uses the same type of cryogen such as, for example, nitrogen. Also, each cryogen source 102 and 104 is in fluid communication with a cryosurgical instrument 106.

Gaseous cryogen source 102 may be a cylinder that is connected to the cryosurgical instrument 106 by a first liquid gas pathway that includes, in series, a fluid gas connector line 110 connected to a first two-way gas valve 109, and a gas connector 108 featuring a second two-way gas valve 112, and which is then in fluid communication with an inlet lumen 116 of cryosurgical instrument 106.

Liquid cryogen source 104 is connected to the cryosurgical instrument 106 through a second gas pathway that includes, in series, a fluid liquid connector line 118 a liquid two-way valve 120 and which is then in fluid communication with inlet lumen 116 of cryosurgical instrument 106. These components in fluid communication with liquid cryogen source 104 transport a two phase fluid, having both liquid and gas components.

Cryogen sources 102 and 104 do not supply cryogen to the tip 124 of the cryoprobe 106 simultaneously. The selection of the appropriate source 102 or 104 is achieved by selective operation of two-way valves 112 and 120.

To heat the tip 124, gaseous cryogen from cryogen source 102 is delivered to and enters the inlet lumen 116 and flows to and is warmed by a heating element 126. The temperature of heating element 126, and hence of the gaseous cryogen, is preferably controlled by a thermocouple 128, which senses the temperature of the gaseous cryogen and which is in electrical communication with heating element 126. In more detail, the thermocouple 128 provides feedback as to the temperature of the heated cryogen, which can be used to regulate operation of the heating element 126. For example, when the heating element is of an electrically resistive type, feedback from the thermocouple may be used to regulate the amount of current flowing to the heating element. Other ways to control the heating, not shown, can be achieved either by placing the thermocouple at the exhaust lumen 119 outside the cryosurgical probe, or measuring the resistance of the electrical element.

Since the cryogenic fluid is the same in sources 104 and 102, the gaseous phase from the top of the liquid phase from source 104 can fill source 102 through connecting line 129 and valve 130.

For safety reasons, optionally gas cryogen source 102 also features a pressure meter 184 for determining internal pressure.

Thus, as illustrated, there are two discrete sources of the same cryogen, one source supplying the cryogen in a liquid state (104) and the other source supplying the cryogen in a gaseous state (102). In operation, these cryogen sources, in cooperation with the heating element 126, provide both selective cooling and heating of the cryosurgical instrument 106. In more detail, gaseous cryogen from gaseous source 102 is selectively heated by the heating element 126 when heating of the cryosurgical instrument 106 is desired.

Figure 2:
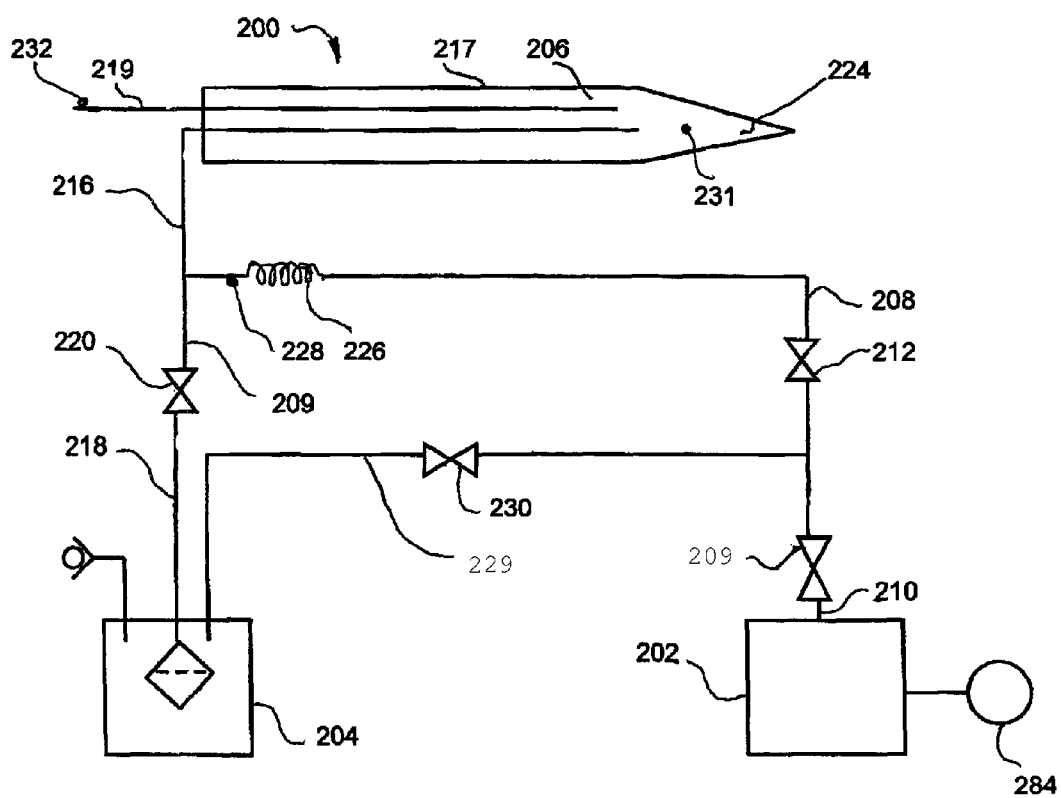
FIG. 2 is a schematic diagram of a cryosurgical system with cryosurgical instrument consistent with an embodiment of the present invention, in which the heating element is outside of the cryosurgical instrument.

Referring to FIG. 2, there is illustrated a system 200 comprising a gaseous cryogen source 202, a liquid cryogen source 204, and a cryosurgical instrument 206. Much of the arrangement of system 100 is shared by system 200.

Each cryogen source 202 and 204 uses the same cryogen such as, for example, nitrogen. Also, each cryogen source 202 and 204 is in fluid communication with a cryosurgical instrument 206.

One difference between systems 100 and 200, however, is that a heating element 226 is located outside of cryosurgical instrument 206. As illustrated, the heating element 226 may be located in-line to gas connector 208 downstream from the gaseous cryogen source 202. For example, heating element 226 is optionally located before the fluid connection to inlet lumen 216. Again, heating element 226 may be an electrical (resistance) heating element. Other heating arrangements are both possible and contemplated. For example, additionally and/or alternatively, the heating element 226 may be a piezoelectric element sensitive to a user's grip.

In system 200, a thermocouple 228 may also be located in-line to gas connector 208. As illustrated in FIG. 2, the thermocouple 228 may be located after heating element 226. This thermocouple 228 may, however, be located in other locations upstream of the inlet lumen 216.

Optionally, one or more additional thermocouples may be provided. For example there may optionally be two such additional thermocouples as shown, including a thermocouple 231 at tip 224 and also a thermocouple 232 at exhaust lumen 219.

Thus, as illustrated, there are two discrete sources of the same cryogen, one source supplying the cryogen in a liquid state (204) and the other source supplying the cryogen in a gaseous state (202). In operation, these cryogen sources, in cooperation with the heating element 226, provide both selective cooling and heating of the cryosurgical instrument 206. In more detail, gaseous cryogen from gaseous source 202 is selectively heated by the heating element 226 when heating of the cryosurgical instrument 206 is desired. The gas is heated upstream of the inlet lumen 216.

Figure 3:
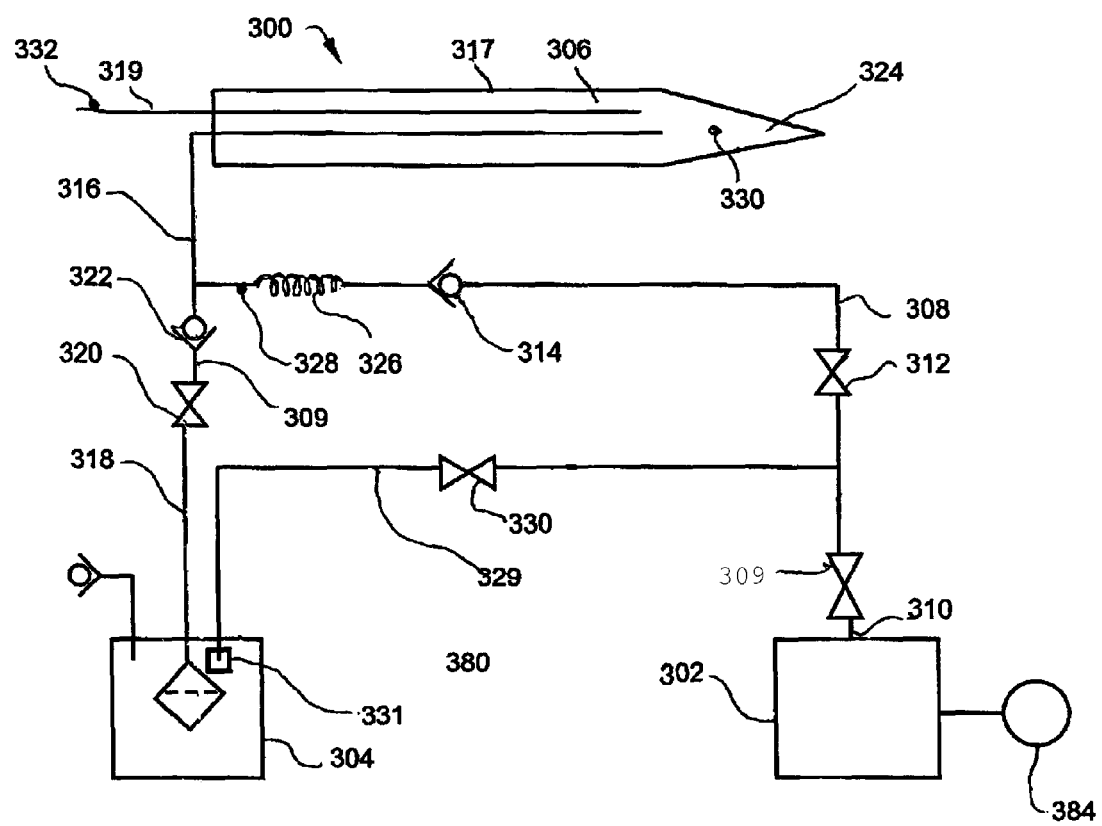
FIG. 3 is a schematic diagram of a system consistent with an embodiment of the present invention, in which the gaseous phase from the two phase "liquid" cryogen source is shifted to the gas cryogen source and or the liquid phase is heated to fill the gaseous source.

Referring to FIG. 3, there is illustrated a system 300 comprising a gaseous cryogen source 302, a liquid cryogen source 304, and a cryosurgical instrument 306. Much of the arrangement of system 200 is shared by system 300.

Each cryogen source 302 and 304 uses the same cryogen such as, for example, nitrogen. Also, each cryogen source 302 and 304 is in fluid communication with a cryosurgical instrument 306.

One difference between systems 200 and 300 is the transfer of the gaseous phase from the liquid cryogen source 304 to the gaseous cryogen source 302. This gaseous phase is generated by heating the gaseous phase with an electrical heater 331 in or adjacent to the liquid cryogen source 304. As illustrated, the electrical heater 331 is preferably placed within liquid cryogen source 304. Additionally and/or alternatively, the heating element 331 may be either immersed in the liquid phase in direct contact with the general volume of the liquid cryogen, or inserted into small vessel (not shown) within the liquid cryogen source 304. This small vessel may be connected by line 329 to the gaseous cryogen source 302. Optionally and preferably, electrical heater 331 does not surround fluid liquid connector line 318, nor is electrical heater 331 placed in-line with fluid liquid connector line 318.

Advantageously, the electrical heater 331 may be selectively activated and/or deactivated according to detected performance/operational parameters such as, by way of non-limiting examples, pressure, as recorded by pressure meter 384, temperature, timing (for example according to those periods that the cryogen flows from liquid cryogen source 304) or a combination thereof.

In operation, the heating element 331, in the liquid cryogen source 304 heats a portion of the liquid cryogen therein and transforms it to gas. The additional heat energy results in increasing the pressure in the liquid cryogen source 304, which encourages the transfer of the gaseous phase to the gaseous cryogen source 302. The generated gaseous phase is transmitted between the cryogen sources 302 and 304 via line 329 and line 309 by selective operation of valves 330 and 322.

The size and type of the heating element 331 may depend on the speed of obtaining the desire pressure. One advantageous example for implementation of heating element 331 is an insulated electrical type heating element that uses between 250-1000 watts.

Without wishing to be limited by a closed list, the inventors have found that such an element effectively increases the pressure in the liquid cryogen source 304 to up to 100 psi in reasonably short time, on the order of minutes. The increase in pressure generally elevates the boiling temperature of the cryogen. A benefit of using electrical heater 331 to increase the pressure in the liquid cryogen source 304 is the simplicity of the use of available power source, which directly transforms energy into pressure. Another requirement is that less time is required, as well as the ease of control versus a pump for the same purpose. Pumping gaseous cryogen between the cryogen sources 302 and 304 would require a pump and additional piping, which is avoided by using the heating element 331.

In more detail, the heater 331 in system 300 is used to raise the pressure in the liquid cryogen sources 304 and 302 by boiling the liquid cryogen stored therein, until the pressure reaches a specified threshold as measured by pressure gauge 384. It is done by keeping valves 330 and 309 open, and valves 312 and 320 closed. A particularly advantageous threshold may be, for example, between about 40-100 psi.

For thawing mode of operation, another heating element 326 is located outside of cryosurgical instrument 306 and also outside of gaseous cryogen source 302. As illustrated, the heating element 326 may be located in-line to gas connector 308 downstream from the gaseous cryogen source 302. For example, heating element 326 is optionally located after one way valve 314. Again, heating element 326 may be an electrical (resistance) heating element. Other heating arrangements are both possible and contemplated. For example, additionally and/or alternatively, the heating element 326 may be a piezoelectric element sensitive to a user's grip.

In system 300, to monitor the heating of the gaseous phase during active thawing, a thermocouple 328 may also be located in-line to gas connector 308. As illustrated in FIG. 3, the thermocouple 328 may be located after heating element 326. This thermocouple 328 may, however, be located in other locations upstream of the inlet lumen 316. The location of the thermocouple 328 monitoring the heating may also optionally be located, at the tip 330, while the position of thermocouple 332 may also optionally be located at the return/exhaust line 319.

Thus, as illustrated, there are two discrete sources of the same cryogen, one source supplying the cryogen in a liquid state (304) and the other source supplying the cryogen in a gaseous state (302). In operation, these cryogen sources, in cooperation with the heating element 326, provide both selective cooling and heating of the cryosurgical instrument 306. In more detail, gaseous cryogen from gaseous source 302 is selectively heated by the heating element 326 when heating of the cryosurgical instrument 306 is desired. The gas is heated upstream of the inlet lumen 316. To provide additional gaseous cryogen and to assist with this process, the transfer of the gaseous phase from the liquid cryogen source 304 to the gaseous cryogen source 302 is optionally and preferably generated by heating the gaseous phase with an electrical heater 331 in or adjacent to the liquid cryogen source 304.

Figure 4:
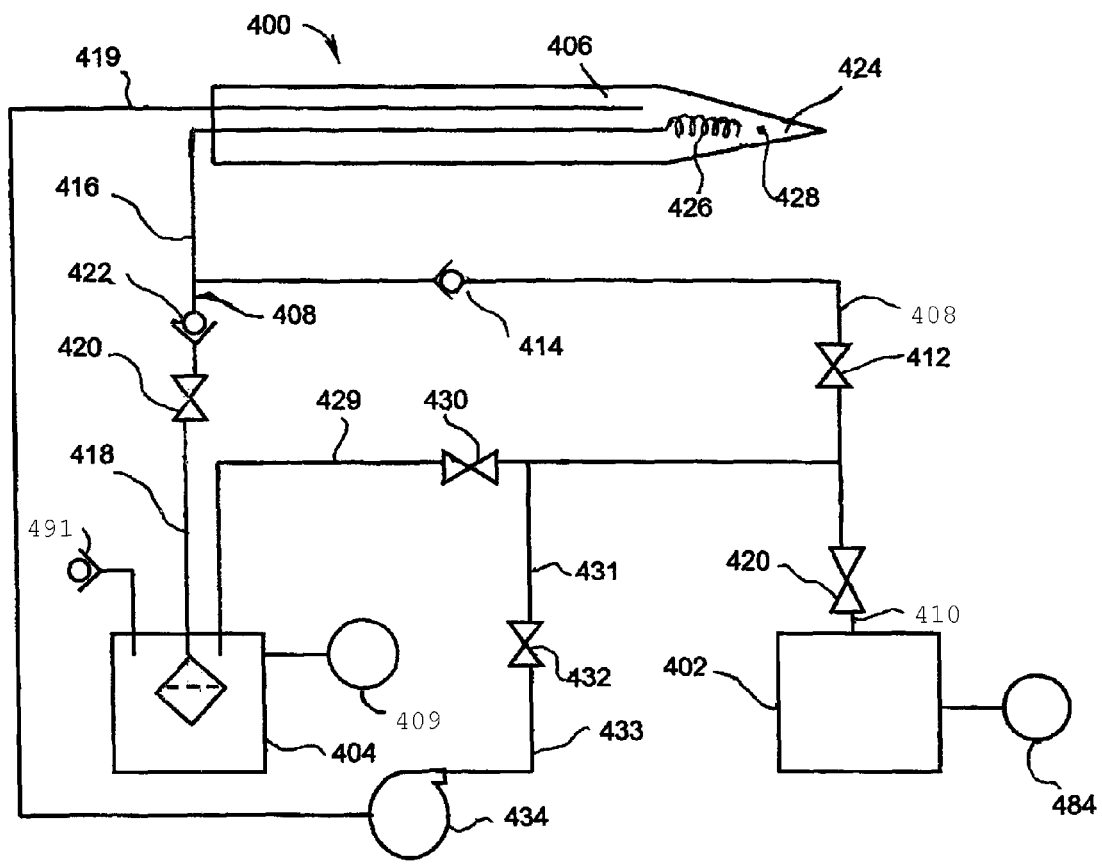
FIG. 4 is a schematic illustration of a cryosurgical system consistent with an embodiment of the present invention, in which the gaseous phase of the cryogen is recycled by transferring the return cryogen to either the liquid/two phase cryogen source, or the gas cryogen source.

Referring to FIG. 4, there is illustrated a system 400 comprising a gaseous cryogen source 402, a liquid cryogen source 404, and a cryosurgical instrument 406. Much of the arrangement of system 100 is shared by system 400. The freeze/thawing cycles provided through alternating application of liquid cryogen and gaseous cryogen as described for the system of FIG. 1 is also provided by system 400. However, system 400 also features, as described below, a recycling solution to enable additional gaseous cryogen to be returned to gaseous cryogen source 402, thereby advantageously "topping up" the supply of gaseous cryogen in gaseous cryogen source 402.

One difference between system 100 and 400 is an exhaust lumen 419 through which the gas phase is returned after the liquid (two phase) cryogen has boiled to cool the tip 424. The returned gas phase is used to fill the gaseous cryogen in gas cryogen source 402 by pumping the returned gas phase with a pump 434 through a pump connector line 433 and another pump connector line 431, as regulated by a two way valve 432.

In system 400, the pump 434 compresses the return cryogen from line 419 and returns it to the liquid cryogen source 404 via lines 433, 431 and 429 by opening the valves 432 and 430. This operation increases the pressure in the liquid cryogen source 404. Additionally and/or alternatively the pump 434 of system 400 increases the pressure in the gaseous cryogen source 402 by compressing the return fluid in line 419, and transferring it to the gaseous cryogen source 402 via lines 433 and 431, and 410, by opening valves 432 and 420.

A pressure gauge 409 preferably controls the activity of the pump 434, for example by turning the pump 434 off and on, so that if pressure at liquid cryogen source 404 reaches a certain threshold, pump 434 is turned off and/or relief valve 491 is opened. As a non-limiting example, the preferred pressure range is 40 psi to 100 psi for liquid nitrogen, but this range is preferably adjusted for other types of cryogens.

A complete recycling solution, for active thawing is provided by system 400. During this mode of operation, valves 432 and 412 are open and valves 430 and 420 are closed. The gaseous cryogen is circulated by the pump through the lines 433, 431, 408, 416, and 419.

Figure 5A:
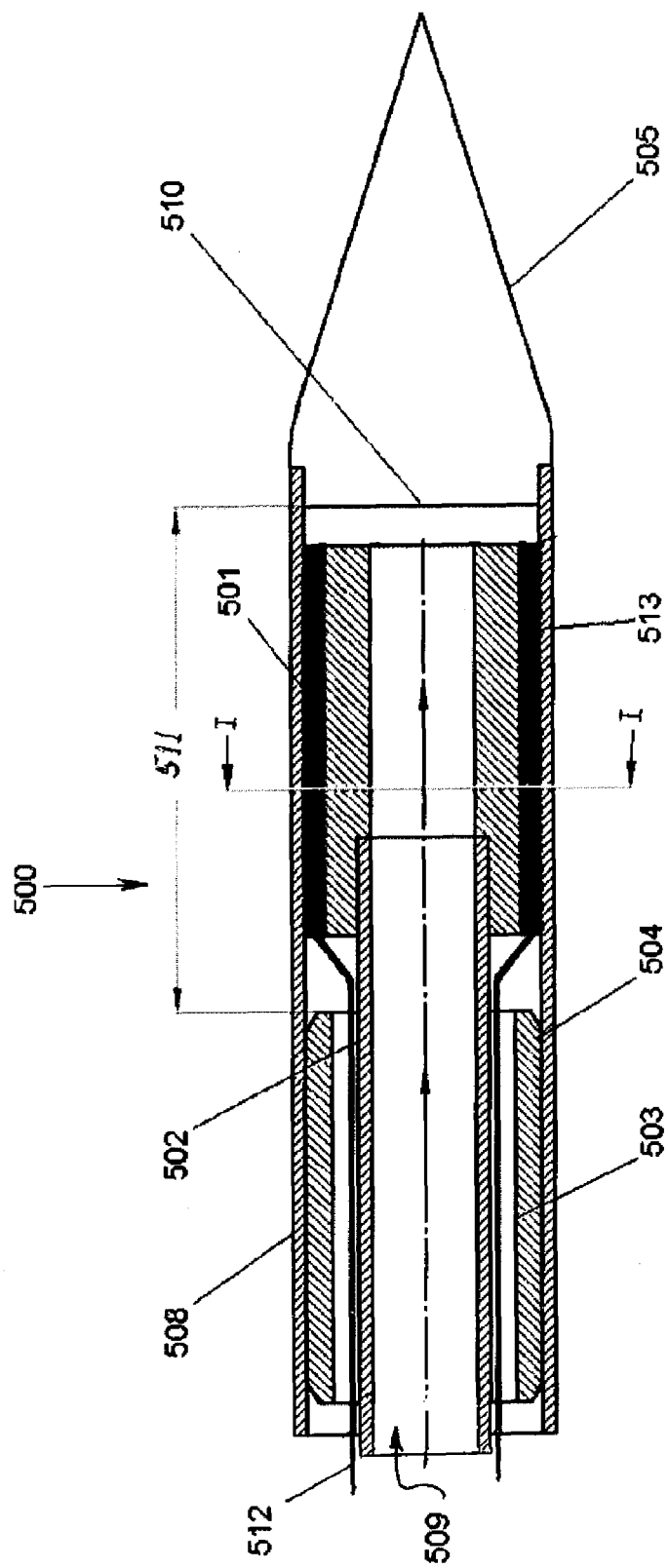
FIG. 5a is a longitudinal cross-sectional view of a first exemplary cryosurgical instrument usable in the system of FIG. 1.
Figure 5B:
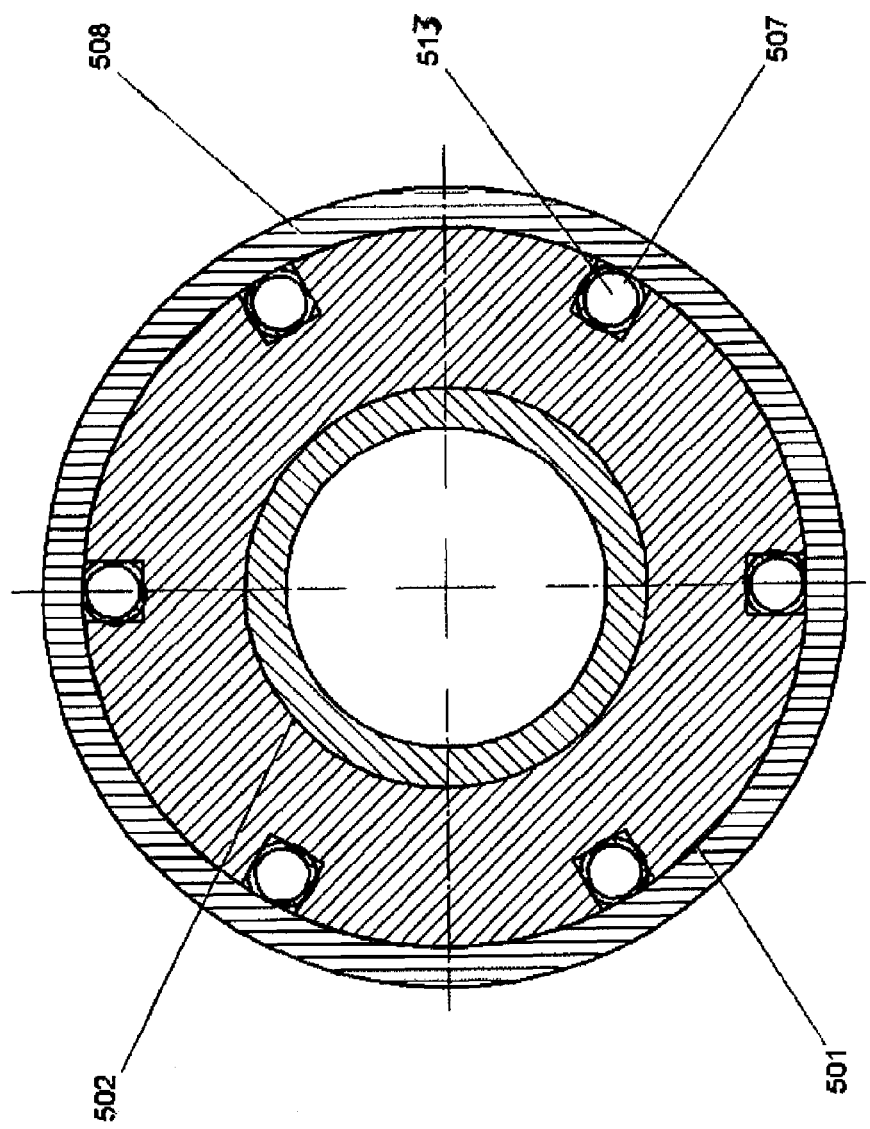
Figure 5C:
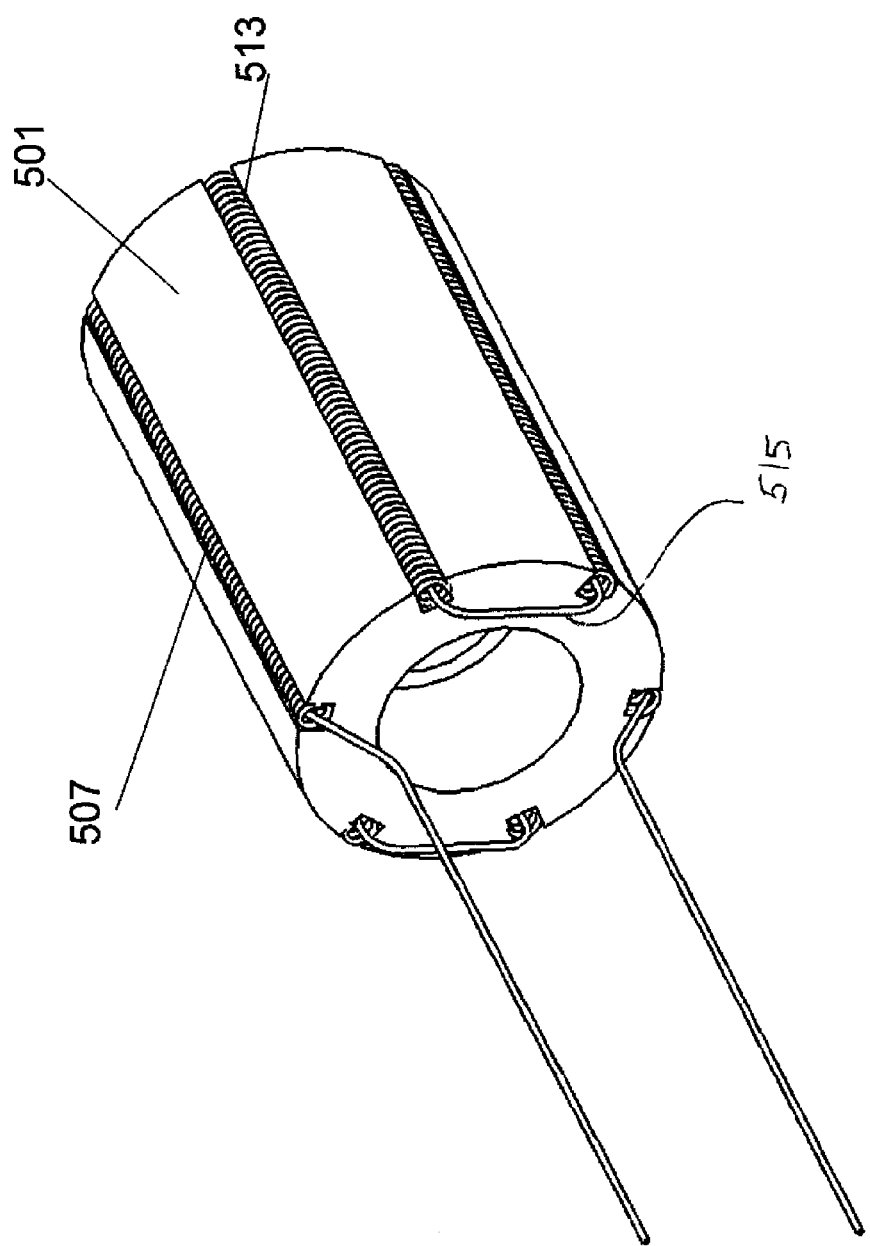

Turning to FIGS. 5a-5c, there is illustrated an example of a cryosurgical instrument 500 usable with any of the systems 100, 200, 300, or 400. Cryosurgical instrument 500 includes an outer shaft 508 that features insulation 504 and an inlet 509 through which fluid and gaseous cryogen flows, according to the source from which cryogen is flowing as previously described, to an inner shaft 509. The cryogen is then reflected by a reflecting surface 510, which is preferably located at, but spacedly separated from, a tip 505, which is a closed and preferably a solid tip. The reflected cryogen then rapidly enters and flows through a plurality of exhaust grooves 507 (shown in FIGS. 5B and 5C) of a heat exchange enhancing element 501. Grooves 507 are preferably straight grooves and function as a plurality of return channels for receiving the expanded return cryogen. Grooves 507 are preferably in communication with an outlet 503 for then exhausting the cryogen out of cryosurgical instrument 500. Grooves 507 may be circumferentially disposed about the longitudinal axis of heat exchange enhancing element 501.

During the freezing part of the operation, the liquid cryogen enters inlet 509 and travels through inner shaft 509. The liquid cryogen is then reflected by reflecting source 510 and travels through exhaust grooves 507. A heat transfer zone 511, shown by arrows, is defined by the boundaries of thermal insulation 504. Heat transfer zone 511 causes tip 505 to be chilled and hence an ice ball to form.

During the thawing part of the operation, the gaseous cryogen enters inlet 509 and travels as for the liquid cryogen. While flowing through the exhaust grooves 507, a heating element 515 heats the gaseous cryogen that, in turn, heats the shaft 508 (in contact with the tissue) and increases the rate of flow through grooves 507. The gaseous cryogen then exits through outlet 503.

As FIGS. 5b and 5c show, the heating element 515 may be an electrical heating coil element with a plurality of coils disposed within the grooves 507 of heat exchange enhancing element 501. As shown, grooves 507 are disposed about the exterior of heat exchange enhancing element 501. Power may be supplied to the heating element 515 through electrical lines 512 (shown also in FIG. 5a). Coils 513 are preferably covered such that only heat is transferred therethrough.

As described above thermal insulation 504 terminates the heat transfer from the cryosurgical instrument 500, thereby defining the end of heat transfer zone 511, in which heat is absorbed from the external environment at heat exchange zone 511.

As explained above, the above construction increases the speed of the return flow. By increasing the speed of the return flow, heat exchange between the shaft 508 at the heat exchanging zone 511 is improved. The heating coils placed in the grooves 507 heat the gaseous cryogen transmitting the heat directly to the shaft 508, and indirectly by conducting the heat through the surface in contact of heat exchange enhancing element 501, resulting in defreezing of an ice ball generated at the heat exchanging zone 511.

Figure 6A:
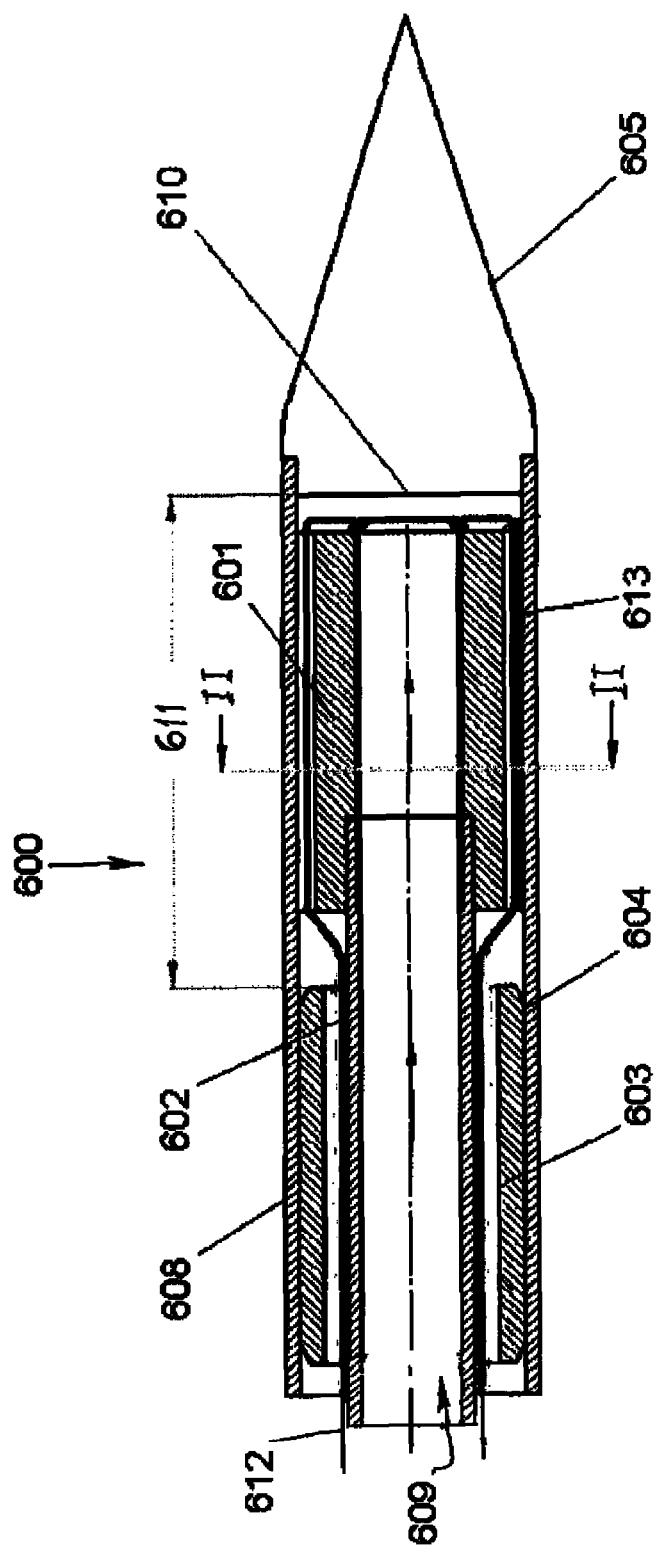
FIG. 6a is a longitudinal cross-sectional view of a second exemplary cryosurgical instrument usable in the system of FIG. 1.
Figure 6B:
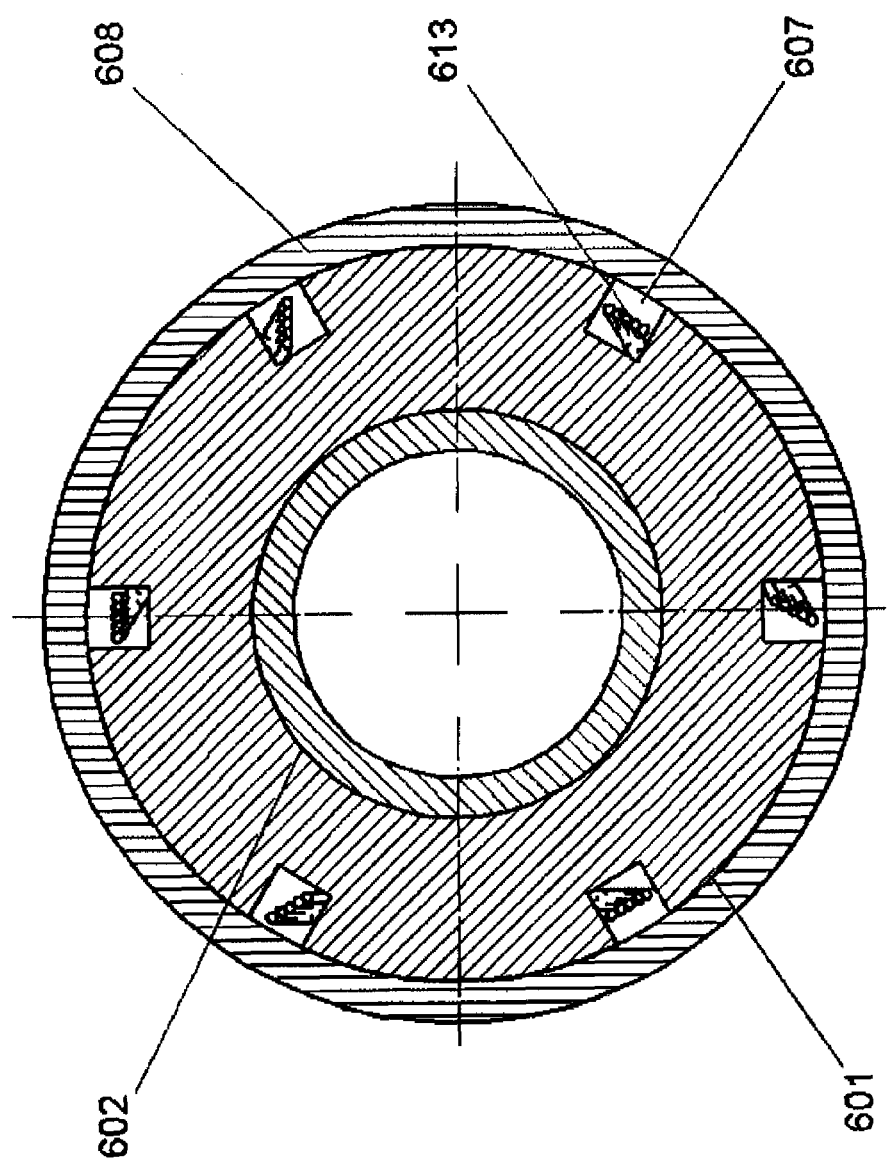
Figure 6C:
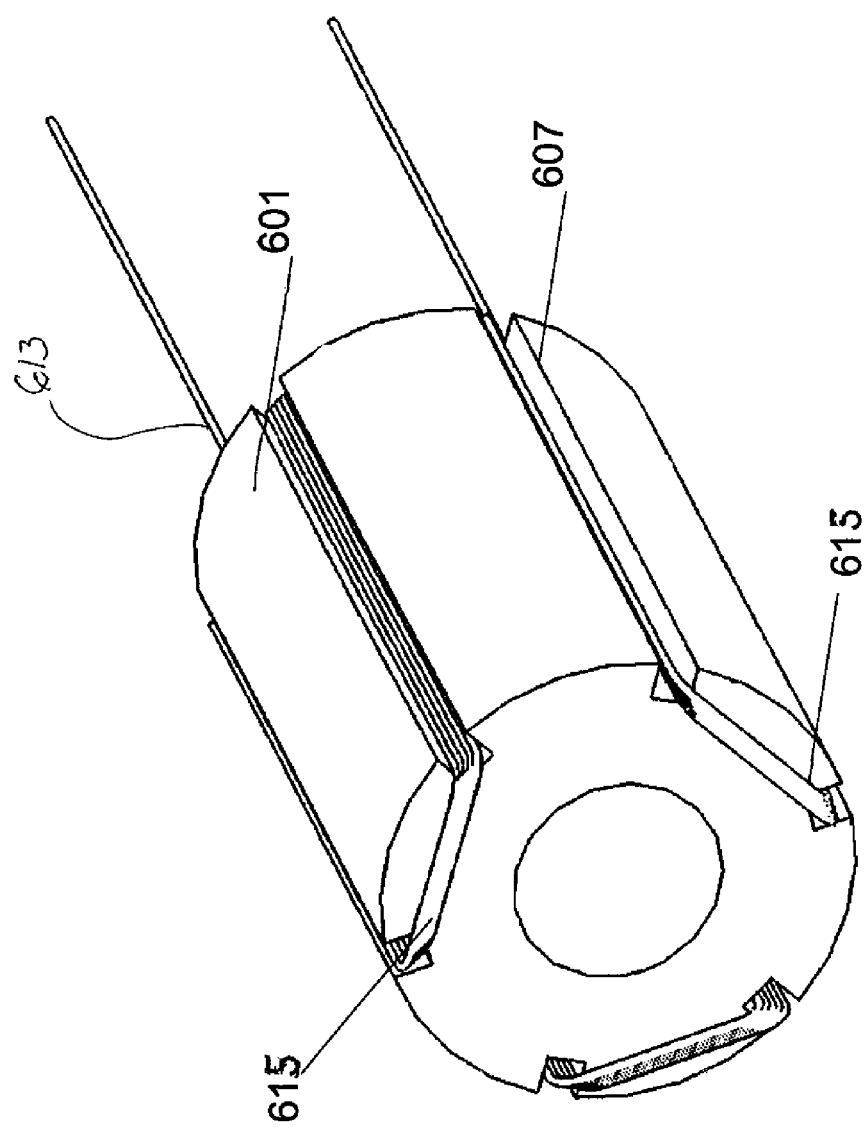
FIG. 6c is a perspective view of a heat exchanging element of the cryosurgical instrument of FIG. 6A.

Turning to FIGS. 6a-6c, there are illustrated an example of a cryosurgical instrument 600 usable with any of the systems 100, 200, 300 or 400. Cryosurgical instrument 600 has many of the same features as the cryosurgical instrument of FIGS. 5a-5c, and elements with the same or similar function have the same number plus 100. The function of cryosurgical instrument 600 is also highly similar to that of cryosurgical instrument 500. However, preferably wires 613 are arranged such that a plurality of wires 613 run in parallel in each groove 607, to create one long resisting electrical element, which is heated by electrical current.

As FIG. 6c illustrates, the wire 613 is shown laid along grooves 607, wrapping the heat exchange enhancing element 615 like the rotor of an electrical engine.

Figure 7A:
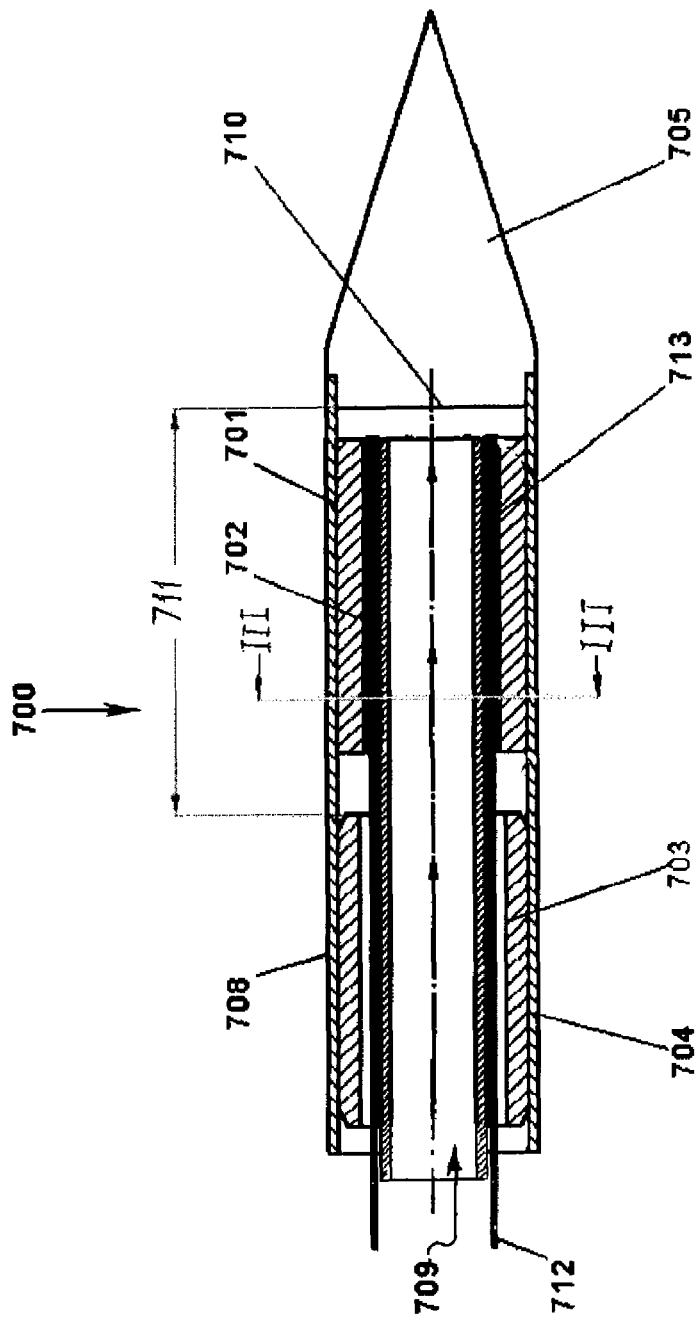
FIG. 7a is a longitudinal cross-sectional view of a third exemplary cryosurgical instrument usable in the system of FIG. 1.
Figure 7B:
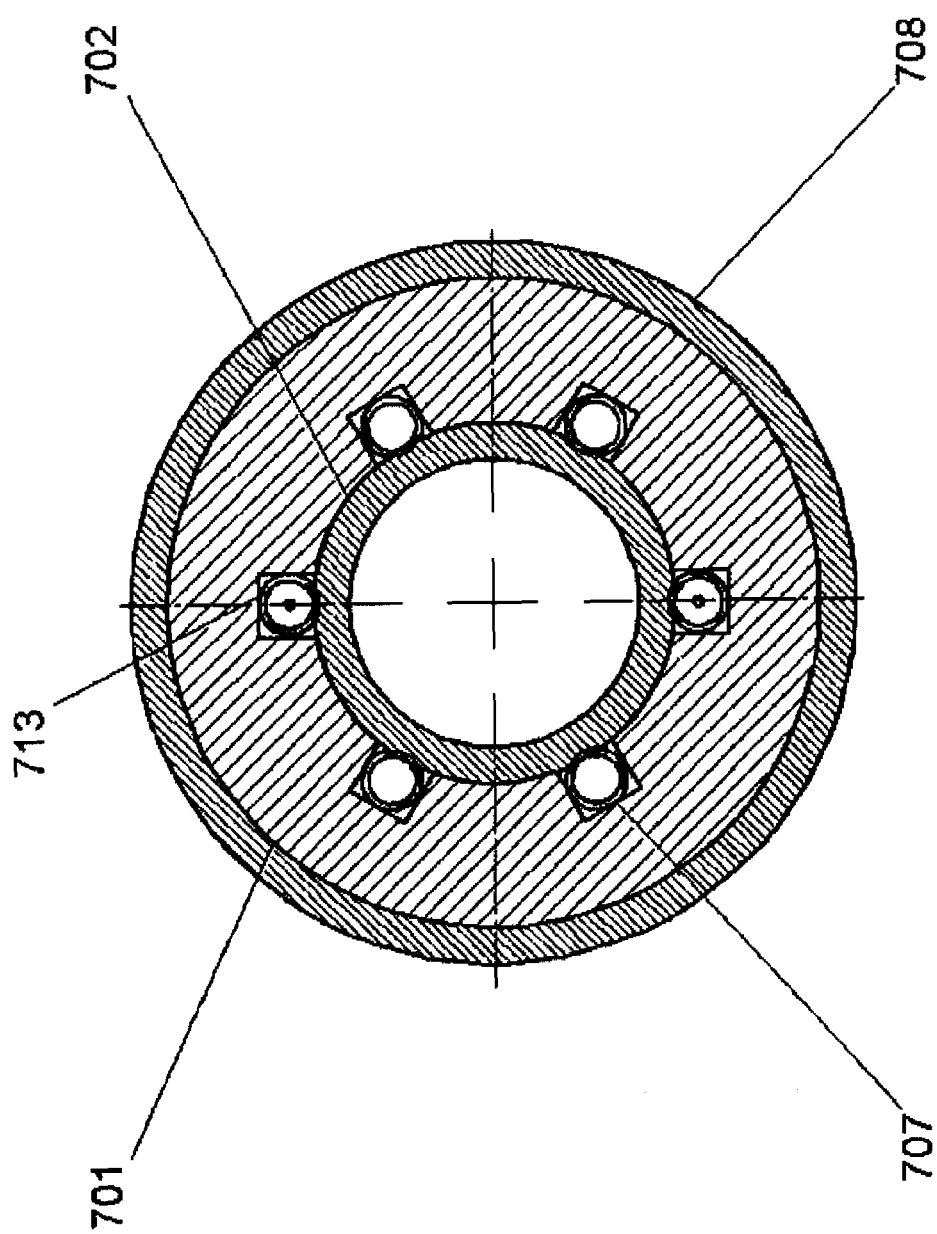
Figure 7C:
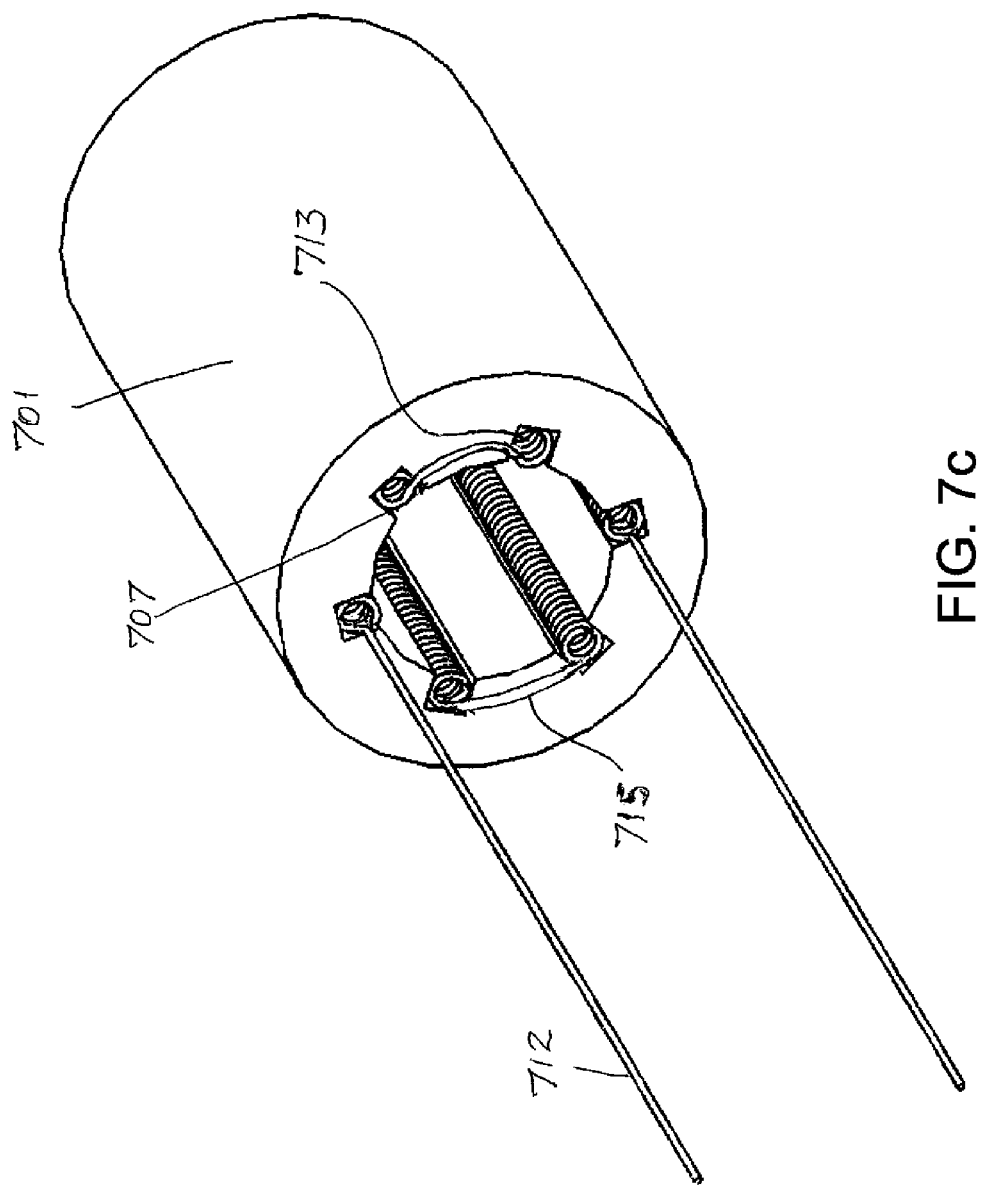

Turning to FIGS. 7a-7c, there is illustrated an example of a cryosurgical instrument 700 usable with any of the systems 100, 200, 300 or 400. Cryosurgical instrument 700 has many of the same features as the cryosurgical instrument of FIGS. 5a-5c, and elements with the same or similar function have the same number plus 200. The function of cryosurgical instrument 700 is also highly similar to that of cryosurgical instrument 500. However, preferably grooves 707 are located in the interior of heat exchange enhancing element 701, but external to the internal cryogen supply passage. Wires 713 are preferably located as coils within grooves 707.

Figure 8:
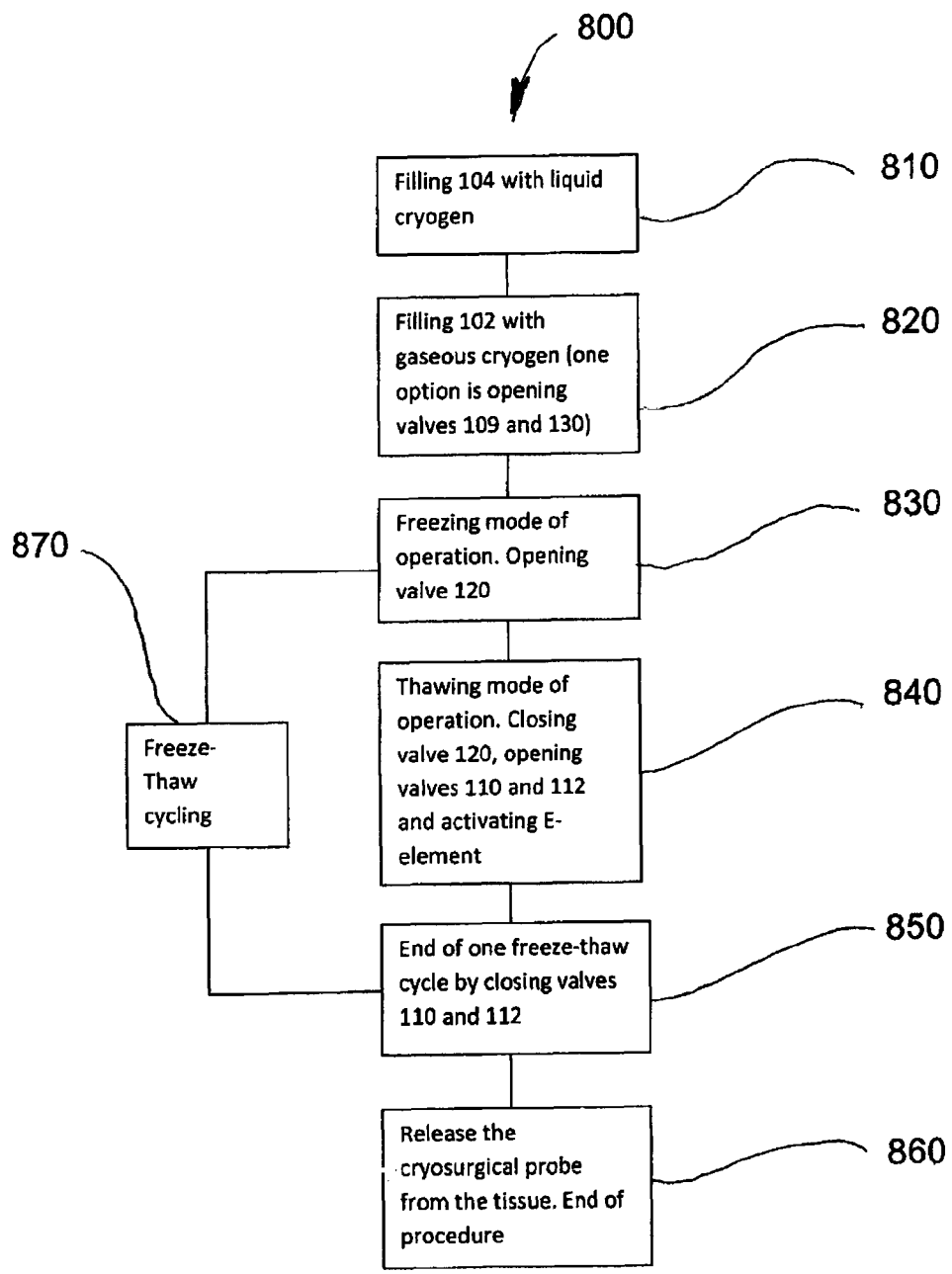
FIG. 8 is a flowchart of an exemplary, illustrative method of treatment using the system of FIG. 1.

FIG. 8 illustrates a method 800 of performing cryosurgical ablation. In the description of method 800 that follows, concurrent reference is made to the system 100 of FIG. 1. This concurrent reference is merely to facilitate understanding of the method 800. It is to be understood that the method need not be used with system 100 and is usable by systems with other configurations.

In operation 810, a cryogen, in liquid state, fills a liquid cryogen source/reservoir (104). In operation 820, the cryogen, in a gaseous state, is delivered to a gaseous cryogen source/reservoir (102). Next, in operation 830, a tip (124) of the cryosurgical instrument, which is in communication with the cryogen sources/reservoirs, is inserted into target tissue in preparation for cryoablation. The cryoablation process of method 800 consists of one or more two-step cycles of freezing and thawing. In operation 840, the tip is cooled by a flow of cold liquid cryogen. In operation 850, the tip is warmed by a flow of warmed gaseous cryogen.

In operation 860, it is determined whether the two-step freezing/thawing cycle should be repeated. When it is determined that the two-step cycle should be repeated, the method returns to operation 830. When it is determined that the two step cycle should not be repeated, the method continues to operation 860, in which the cryosurgical instrument is warmed by a flow of warm gaseous cryogen so as to facilitate release from the target tissue.

Operations 840-860 may be repeated until a desired cryoablation result is achieved.

As the foregoing illustrates, the embodiment(s) provide a cooling and heating options utilizing a single cryogen delivered from a source of liquid cryogen and a source of gaseous cryogen. The liquid cryogen cools the tip of a cryosurgical instrument, such as a cryosurgical instrument or cryocatheter. The gaseous cryogen is heated by a heating element, preferably an electrical heating element, heating the tip.

Examples of various features/aspects/components/operations have been provided to facilitate understanding of the disclosed embodiments of the present invention. In addition, various preferences have been discussed to facilitate understanding of the disclosed embodiments of the present invention. It is to be understood that all examples and preferences disclosed herein are intended to be non-limiting.

Although selected embodiments of the present invention have been shown and described individually, it is to be understood that at least aspects of the described embodiments may be combined.

Also although selected embodiments of the present invention have been shown and described, it is to be understood the present invention is not limited to the described embodiments. Instead, it is to be appreciated that changes may be made to these embodiments without departing from the principles and spirit of the invention, the scope of which is defined by the claims and the equivalents thereof.

What is claimed is:

1. A cryosurgical system, comprising:
   a cryosurgical instrument including a tip that is cooled by a cryogen in a fluid state and warmed by a same type of cryogen in a heated gaseous state;
   a fluid cryogen source that supplies a liquid cryogen to the cryosurgical instrument;
   a gaseous cryogen source that supplies a gaseous cryogen to the cryosurgical instrument; and
   a heating element that selectively heats the gaseous cryogen, wherein the gaseous cryogen and the fluid cryogen are not supplied to the cryosurgical instrument simultaneously but rather are supplied sequentially, such that wherein said fluid cryogen source is in fluid communication with the cryosurgical instrument, said gaseous cryogen source is not in fluid communication with the cryosurgical instrument; and such that wherein said gaseous cryogen source is in fluid communication with the cryosurgical instrument, said fluid cryogen source is not in fluid communication with the cryosurgical instrument, and
   wherein the gaseous cryogen source and the liquid cryogen source supply a same type of cryogen.

2. The system of claim 1, wherein the cryosurgical instrument, the fluid cryogen source and the gaseous cryogen source comprise a closed system.

3. The system of claim 2, wherein the fluid cryogen source is in gaseous communication with the gaseous cryogen source and cryogen in a gaseous phase in the liquid cryogen source is delivered to the gaseous cryogen source.

4. The system of claim 3, wherein the fluid cryogen source includes a cryogen heater that heats and converts liquid cryogen into gaseous cryogen.

5. The system of claim 1, wherein a gas phase of cryogen exhausted from the cryosurgical instrument is delivered to the gaseous cryogen source.

6. The system of claim 1, wherein the heating element is upstream of the cryosurgical instrument.

7. The system of claim 1, wherein the heating element is upstream of a section at which the gaseous cryogen and the liquid cryogen comingle before being supplied to the cryosurgical instrument.

8. The system of claim 1, further comprising a heat exchange enhancing element disposed in the cryosurgical instrument near the tip and in a heat exchange zone, the enhancing element having a plurality of external cryogen return grooves circumferentially disposed lengthwise along the enhancing element.

9. The system of claim 8, further comprising a heating element disposed in the grooves.

10. The system of claim 9, wherein said grooves are disposed lengthwise along an internal passage of the enhancing element, or lengthwise along an external passage of the enhancing element.

11. The system of claim 9, wherein the heating element is an electrical heating coil element with (i) a plurality of coils disposed in the grooves or (ii) a plurality of wires disposed in the grooves and running several times in each groove so as to create one long resisting electrical element.

12. The system of claim 11, wherein said coils are insulated.

13. A cryosurgical system, comprising:
   a first source of a cryogen, the first source providing the cryogen is a gaseous phase;
   a second source of the cryogen, the second source providing the cryogen in a liquid phase;
   a cryogen heating section that selectively heats provided gaseous phase cryogen; and
   a cryosurgical instrument having a tip and receiving provided cryogen in a two-phase state,
   wherein the provided cryogen in the liquid phase cools the tip,
   wherein the provided cryogen, after being heated by the heating section, warms the tip, and
   wherein the heating and cooling of the tip are achieved using only the provided cryogen.

14. A system, comprising:
   a cryosurgical instrument having a tip;
   a first container storing a cryogen in a gaseous state;
   second container storing the cryogen in a liquid state; and a gaseous cryogen heater that selectively heats the gaseous cryogen as it travels from the first container to the cryosurgical device, wherein the heated gaseous cryogen is joined with liquid cryogen as it travels to the cryosurgical device, and wherein the liquid cryogen and heated gaseous cryogen cooperate to selectively heat and/or cool the tip.

15. A cryosurgical system, comprising:

a cryosurgical instrument having a tip that is warmed by heated gaseous cryogen and cooled by liquid cryogen;

means for supplying a cryogen in a gaseous phase;

means for supplying the cryogen in a liquid phase;

means for mixing together supplied gaseous cryogen and supplied liquid cryogen so as to deliver to the cryosurgical instrument a two phase cryogen that includes cryogen in both liquid and gaseous phases; and means for selectively heating the gaseous cryogen.

\* \* \* \* \*